(12) United States Patent
Savolainen et al.

(10) Patent No.: US 9,221,861 B2
(45) Date of Patent: Dec. 29, 2015

(54) MULTIVALENT [BETA]-1-2-LINKED MANNOSE OLIGOSACCHARIDES AS IMMUNOSTIMULATORY COMPOUNDS AND USES THEREOF

(75) Inventors: Johannes Savolainen, Turku (FI); Kaarina Mäkinen, Pori (FI); Reko Leino, Piispanristi (FI); Chinmoy Mukherjee, Andhra Pradesh (IN)

(73) Assignees: ABO AKADEMI UNIVERSITY, Turku (FI); TURUN YLIOPISTO, Turun Yliopisto (FI)

(*) Notice: Subject to any disclaimer, the term of this patent is extended or adjusted under 35 U.S.C. 154(b) by 8 days.

(21) Appl. No.: 14/128,464

(22) PCT Filed: Jun. 21, 2012

(86) PCT No.: PCT/FI2012/050650
§ 371 (c)(1),
(2), (4) Date: Dec. 20, 2013

(87) PCT Pub. No.: WO2012/175813
PCT Pub. Date: Dec. 27, 2012

(65) Prior Publication Data
US 2014/0105932 A1    Apr. 17, 2014

Related U.S. Application Data

(60) Provisional application No. 61/499,229, filed on Jun. 21, 2011.

(30) Foreign Application Priority Data

Jun. 21, 2011  (FI) ..................... 20115631

(51) Int. Cl.
| C07H 15/26 | (2006.01) |
| A61K 45/06 | (2006.01) |
| A23L 1/30 | (2006.01) |
| A61K 31/7056 | (2006.01) |
| A61K 47/48 | (2006.01) |

(52) U.S. Cl.
CPC . *C07H 15/26* (2013.01); *A23L 1/30* (2013.01); *A61K 31/7056* (2013.01); *A61K 45/06* (2013.01); *A61K 47/48061* (2013.01)

(58) Field of Classification Search
None
See application file for complete search history.

(56) References Cited

U.S. PATENT DOCUMENTS

2002/0054886 A1  5/2002  Cutler et al.

FOREIGN PATENT DOCUMENTS

| WO | WO 02/09728 A1 | 2/2002 |
| WO | WO 2006/098970 A1 | 9/2006 |
| WO | WO 2007/010084 A2 | 1/2007 |

OTHER PUBLICATIONS

Perez-Balderas, F. et al "Click multivalent homogeneous neoglyconjugates . . . " (2009) pp. 2441-2453.*
Alpe et al., "Synthesis of Cryptococcus neoformans Capsular Polysaccharide Structures. IV. Construction of Thioglycoside Donor Blocks and Their Subsequent Assembly", Journal of Carbohydrate Chemistry, vol. 22, No. 7 & 8, 2003, pp. 565-577.
Ballell et al., "A new chemical probe for the detection of the cancer-linked galectin-3", Org. Biomol. Chem., vol. 4, 2006, pp. 4387-4394 (published online Oct. 30, 2006).
Bentz et al., "Aryldiazirine-Modified Pyroglutamates: Photoaffinity Labels for Glutamate", Synlett, No. 2, 2006, pp. 247-250 (published online Dec. 23, 2005).
Bock et al., "A Study of 13CH Coupling Constants in Hexopyranoses", J.C.S. Perkin II, pp. 293-297 (published Jan. 1, 1974).
Codee et al., "Efficient Installation of β-Mannosides Using a Dehydrative Coupling Strategy", Organic Letters, vol. 7, No. 15, 2005, pp. 3251-3254 (published online Jun. 23, 2005).
Crich et al., "1-Benzenesulfinyl Piperidine/Trifluoromethanesulfonic Anhydride: A Potent Combination of Shelf-Stable Reagents for the Low-Temperature Conversion of Thioglycosides to Glycosyl Triflates . . . ", J. Am. Chem. Soc., vol. 123, 2001, pp. 9015-9020 (published online Aug. 21, 2001).
Crich et al., "Direct Stereoselective Synthesis of β-Thiomannosides", J. Org. Chem., vol. 65, 2000, pp. 801-805 (published online Jan. 16, 2000).
Crich et al., "Enhanced Diastereoselectivity in β-Mannopyranosylation through the Use of Sterically Minimal Propargyl Ether Protecting Groups", J. Org. Chem., vol. 71, 2006, pp. 3064-3070 (published online Mar. 23, 2006).
Crich et al., "Synthesis of the *Salmonella* Type El Core Trisaccharide as a Probe for the Generality of 1-(Benzenesulfinyl) piperidine/Triflic Anhydride Combination for Glycosidic Bond Formation from Thioglycosides", J. Org. Chem., vol. 67, 2002, pp. 4640-4646 (published online Jan. 24, 2002).
De Paz et al., "Synthesis and Biological Evaluation of a Heparin-Like Hexasaccharide with the Structural Motifs for Binding to FGF and FGFR", Eur. J. Org. Chem., 2005, pp. 1849-1858.
Langer et al., "Assembly of dendritic glycoclusters from monomeric mannose building blocks", J. Chem Soc., Perkin Trans. J., 1998, pp. 3913-3915, XP055041430 (published online Jan. 1, 1998).
Matsuda et al., "Synthesis of an 11-cis-locked biotinylated retinoid for sequestering 11-cis-retinoid binding proteins", Can. J. Chem., vol. 84, 2006, pp. 1363-1370 (published online Sep. 27, 2006).
Mourer et al., "Easily Accessible Mono- and Polytopic-Cyclodextrin Hosts by Click Chemistry", Eur. J. Org. Chem., 2008, pp. 5723-5730 (published online Oct. 17, 2008).
Ohlsson et al., "Galabiosyl donors; efficient synthesis from 1,2,3,4,6-penta-O-acetyl-β-D-galactopyranose", Carbohydrate Research, vol. 329, 2000, pp. 49-55.

(Continued)

*Primary Examiner* — Leigh Maier
(74) *Attorney, Agent, or Firm* — Birch, Stewart, Kolasch & Birch, LLP

(57) ABSTRACT

This invention relates to synthetic oligo- or multivalent beta-1-2-linked mannooligosaccharide compounds and to their use for modulating T helper (Th) and T regulatory (Treg) cell-mediated immune responses.

14 Claims, 7 Drawing Sheets

(56) References Cited

OTHER PUBLICATIONS

Perez-Balderas et al., "Synthesis of multivalent neoglycoconjugates by 1,3 dipolar cycloaddition of nitrile oxides and alkynes and evaluation of their lectin-binding affinities", Tetrahedron, vol. 61, 2005, pp. 9338-9348 (published online Aug. 10, 2005).

Pfaendler et al., "Synthesis of Racemic Ethanolamine Plasmalogen", Synthesis, Nov. 1996, pp. 1345-1349.

Ratner et al., "A Linear Synthesis of Branched High-Mannose Oligosaccharides from the HIV-1 Viral Surface Envelope Glycoprotein gp120", Eur. J. Org. Chem., 2002, pp. 826-833, XP055041433.

Soderquist et al., "Hydroboration. 56. Convenient and Regiospecific Route to Functionalized Organosilanes through the Hydroboration of Alkenylsilanes", J. Org. Chem., vol. 45, 1980, pp. 3571-3578.

Zhu et al., "A facile regio- and stereoselective synthesis of mannose octasaccharide of the N-glycan in human CD2 and mannose hexasaccharide antigenic factor 13b", Carbohydrate Research, vol. 337, 2002, pp. 207-215, XP004335946.

\* cited by examiner

CM-C4-2010

CM-C4-2011

CM-C7-2010

MULTIVALENT [BETA]-1-2-LINKED MANNOSE OLIGOSACCHARIDES AS IMMUNOSTIMULATORY COMPOUNDS AND USES THEREOF

CROSS REFERENCE TO RELATED APPLICATIONS

This application is the National Phase of PCT/FI2012/050650 filed on Jun. 21, 2012, which claims priority under 35 U.S.C. 119(e) to U.S. Provisional Application No. 61/499,229 filed on Jun. 21, 2011 and Application No. 20115631 filed on Jun. 21, 2011, in Finland, all of which are hereby expressly incorporated by reference into the present application.

FIELD OF THE INVENTION

The invention relates to immunostimulatory compounds, and to their use for modulating T helper (Th) and T regulatory (Treg) cell-mediated immune responses.

BACKGROUND OF THE INVENTION

Type I immediate atopic allergies are one of the most common health problems in the Western world, and constantly increasing in prevalence (ISAAC 1998). It has been speculated that this increase is associated with the reduced microbial load in the developed societies, which has weakened natural T regulatory (Treg) and type 1 Th (Th1)-cell responses, giving way to enhanced Th2 responses that characterize atopic diseases.

CD4+ T cells (Treg, Th1 and Th2) are the main regulators of allergic immune response. Th2 cells that secrete cytokines such as IL-4, IL-5 and IL-13 are important to development of allergic inflammation by inducing IgE-production by B cells, degranulation of mast cells and recruitment of eosinophils. The regulatory T cells and their cytokine IL-10 also have an important role in down-regulation of Th2-type responses towards allergens. Th1 cells are essential for defense against microbes, in particular intracellular pathogens, and cancer by inducing activation of cytotoxic T (Tc) cells and natural killer (NK) cells. In addition, Th1-type cytokines, including IFN-γ, IL-12 and IL-18, are involved in suppression of allergen-induced Th2-type immune responses. Moreover, in allergen vaccination, there is up-regulation of the cytokines IFN-γ, IL-10 and IL-18, indicating their crucial role in suppressing the allergic inflammation also in vivo.

Recent research has shown that the crucial time for the development of either Th1- or Th2-type immunity is infancy. At birth, there is a weak Th2-type immunity, which in healthy individuals is conversed to a Th1-type response. It is thought that the priming of the immune system by microbial components in the environment and gut microflora (endotoxins, lactobacilli, mycobacteria) is essential in this conversion.

Research has been performed on the effects of microbial components on Th1-Th2 balance. A great deal of effort has been directed towards the search for microbial molecules, which could be used in development of more effective and safer vaccines for immunization against infections and in novel therapeutic approaches to treat autoimmune, atopic, and malignant diseases. Among these molecules are 3-deacylated monophosphoryl lipid A (MPL), the non-toxic derivative of lipopolysaccharide of *Salmonella minnesota* (LPS), and immunostimulatory bacterial DNA sequences (CpG-ODN) that generally consist of a central nonmethylated CG di-nucleotide. These molecules have been clinically tested and shown to be effective and well-tolerated adjuvants in a number of vaccines for immunization against and treatment of hepatitis B virus, human immunodeficiency virus (HIV), influenza A virus, and *Plasmodium falciparum*, as well as in treatment of cancers such as non-Hodgkin lymphoma, and melanoma. These molecules have been shown to function by inducing strong Th1-type pattern of cytokine production by acting on various Toll-like receptors on antigen-presenting cells such as monocytes, macro-phages and dendritic cells. Moreover, the Th1-enhancing effects of mycobacteria and bacterial lipopolysaccharide with subsequent suppression of Th2-type response, allergic inflammation, IgE-responses and bronchial hyperreactivity have been shown in several studies. In addition, probiotic lactobacilli have been shown to reduce the prevalence of atopic eczema at the age of two years when administrated orally during pregnancy and immediately after birth. Immunotherapy with bacterial CpG-ODN oligonucleotides bound covalently to allergens has also been shown to decrease the nasal inflammatory response in allergic rhinitis patients. MPL has been successfully tested as an adjuvant in allergen immune-therapy.

The therapeutic use of these microbial compounds faces certain problems. LPS is a toxin and as such unfit for therapeutic use. CpG-ODN is a gene and, in addition to being expensive for large-scale synthesis, implies potential problems with the public opinion (such as gene manipulated food products). MPL adjuvant is not a single chemical entity, but a mixture of analogues, with differences reflected in the number and length of fatty acid chains. Probiotic lactobacilli are live bacteria, comprising safety problems with respect to possible infections, and furthermore are difficult to standardize. Also mycobacterial lysates are crude mixtures of bacterial components out of range of biological standardization. An ideal therapeutic component for allergy treatment would be a naturally occurring, non-toxic, safe purified molecule with as small molecular size as possible.

In WO 02/09728 complex carbohydrates are presented for prevention and treatment of a variety of over 80 diseases. In this publication carbohydrates are defined as any polymer comprising more than two sugar moieties and including such classes of compounds as polysaccharides (that include mucopoly-saccharides and mannans) and oligosaccharides [that are comprised of branched oligosaccharides such as sialylated sugars including milk sugars; the key milk sugars (also called hexaoses) incorporated in the general class of complex carbohydrates being difucosyllacto-N-hexaose a and b, disialyl-monofucosyllacto-N-hexaose and monofucosyllacto-N-hexaose I, II and II]. The diseases listed include conditions associated with allergies; individually mentioned are anaphylaxis, asthma and itching associated with allergies and hypersensitivity and are based on e.g. inhibition of white cell adhesion.

US 2002/0054886 discloses a vaccine, comprising β-1,2-linked straight chain oligo-mannosyl residues for the treatment of candidiasis. The oligo-mannosyl residues are used as an epitope to elicit a protective antibody response against candidiasis or to prevent *Candida albicans* adhesion to mammalian cells. The effect is based on the use of a synthetic substance mimicking microbial compounds, administrated to induce a specific immune response against the substance.

WO2006/096970 A1 discloses another application for the treatment of candidiasis. Therein are provided conjugates comprising native O-linked and S-linked oligosaccharides, more specifically β-1,2-linked straight chain oligo-mannosyl residues, coupled to a protein carrier via a linker. Said conjugate always comprises a protein. It is essential that said protein carrier elicits a thymus dependent immune response. The synthesis strategy for linking said moieties is presented as well. The conjugate formed of oligosaccharides and protein carrier covalently attached by a linker, is suggested to be usable for inducing an immune response to a *Candida* species in a subject in need thereof.

WO2007/010084 discloses immunostimulatory mannan polysaccharides comprising β-1,2-linked chains and β-1,2-(D)-mannooligosaccharides, and their uses for modulating T helper (Th) cell-mediated immune responses. However, the activity of synthesized simple β-1,2-linked mannooligosaccharide chains consisting of up to four oligosaccharides was inferior as compared to natural crude oligosaccharide mixtures. Therefore, novel modifications of these synthetic oligosaccharide chains were needed.

OBJECT AND SUMMARY OF THE INVENTION

In the ongoing research effort of the inventors, it has been found that synthetic oligo- or multivalent β-1-2-linked mannooligosaccharide compounds have excellent properties for modulating T helper (Th) and T regulatory (Treg) cell-mediated immune responses.

Therefore, one object of the present invention is to provide an immunostimulatory compound and composition for modulating T helper (Th) and T regulatory (Treg) cell-mediated immune responses.

Another object of the present invention is to provide an immunostimulatory compound for use as a medicament. Yet, another object of the present invention is to provide an immunostimulatory compound for use as a medicament for treating a mammal, including human, suffering from or susceptible to a condition which can be prevented or treated by inducing a Treg- and/or Th1-type, and/or inhibiting a Th2-type immune response.

A further object of the present invention is to provide an immunostimulatory compound for use as an adjuvant of a vaccine.

Another further object of the present invention is to provide an immunostimulatory compound for use as a food additive.

To achieve these objects, the invention is characterized in what will be presented in independent claims.

Some preferred embodiments of the invention will be described in the other claims.

Typically, the immunostimulatory compound according to the present invention is an oligo- or multivalent carbohydrate assembly or array where a number of β-1,2-linked mannooligosaccharides are with a linker group connected to a central core unit or carrier. In more detail, the immunostimulatory compound according to the present invention is an oligo- or multivalent β-1,2-linked mannooligosaccharide of formula (I)

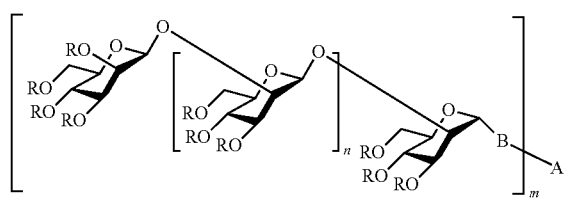

wherein n is from 0 to 6, m is from 3 to 5 and wherein each R is independently selected from acetyl (COCH₃), hydrogen (H), trifluoroacetyl (COCF₃) or sulfonate group or other ester group, and wherein β-1,2-linked mannooligosaccharides are with a linker group (B) connected to a central core unit or carrier (A).

As presented above, the last sugar of formula (I) is alpha-linked to linker/carrier. However, this terminal linkage could also in another lead compound be beta-linked. In other words, with β-1,2-linked mannooligosaccharides it is referred here to compounds where mannose units are coupled to each other by β-1,2-linkages but such oligosaccharides can then be coupled to the carrier via a linker either by β- or α-position.

The inventors have found that immunostimulatory compounds provide good results even when employing different linkers. A man skilled in the art can select a linker suitable for an immunostimulatory compound of the present invention. However, based on experiments conducted, the synthetic immunostimulatory compound according to the invention can for example comprise either a triazole moiety or a derivative thereof, or a carbon chain as a linker group B of the molecule.

Said linker B may preferably consist of a structure:

—X—Y—Z— wherein X is zero or represents group —CH₂—, or atom O, S or N; Y represents a carbon chain, which may optionally be substituted, having a backbone consisting of from 1 to 8 carbon atoms, and is most preferably an aliphatic C₄-C₆ carbon chain; and Z is zero or represents an atom selected from O, S or N. The linker group (B) does, however, not comprise a moiety derived from p-nitrophenyl adipic acid diester or thioacetate pentane.

When B comprises a triazole moiety, the structure above may be presented as:

—X—Y'—Z— wherein X is zero or represents group —CH₂—, or atom O, S, or N, and; Y' represents a triazole moiety, which is bonded to X from 1-nitrogen of said triazole with group —(CH₂)$_p$—, wherein p is from 1 to 10, preferably from 1 to 6, and which Y' is bonded to Z from the 4-carbon of said triazole group with group —(CH₂)$_q$—, wherein q is from 1 to 6, and Z is zero or represents an atom selected from O, S or N. In the experimental part, compounds wherein X is atom O, Y' is group —(CH₂)$_p$— wherein p is 2 or 3, q is 1 and Z is zero, have been synthesized and tested for activity.

The central core unit or carrier A can be a substituted or unsubstituted aliphatic, aromatic or cyclic structure or a polymer, preferably a substituted or unsubstituted aliphatic, aromatic or cyclic structure. When selecting said core unit A from relatively small and simple molecules, the overall structure and size of the immunostimulatory compound remains small respectively. With relatively small and simple molecules is here referred to an aliphatic, aromatic or cyclic structure, wherein core unit A comprises up to 20 carbon molecules, preferably, up to 10 carbon molecules, more preferably up to 6 carbon molecules and most preferably up to 3 carbon molecules in their backbone structure. A person skilled in the art readily comprehends that the size of the core unit has a correlation to the number of the β-1,2-linked mannooligosaccharides attachable thereto via linkers (B). Hence, a core compound comprising three carbon molecules can be via three linkers (B) linked to three β-1,2-linked mannooligosaccharides. With the linking techniques according to the present invention, up to five β-1,2-linked mannooligosaccharide moieties may be linked to a glucopyranose ring as illustrated in FIG. 7b.

In one embodiment, the β-1,2-linked mannooligosaccharide moieties may via linkers be bound/tethered to Silicon (Si)

as carrier, hence for example, showing 9 or 12 carbohydrate moieties. According to yet another embodiment, tyrosine may be used as carrier/depot helper substance.

When desired, one or more substituents to said central core unit or carrier may be selected to provide further functionalities. One or more carbons may be substituted with a group or substituent providing a binding site for linking, attaching or binding said central core or carrier to another similar or different compound, to immobilize it or engineer thereto other functionality or functionalities.

An oligo- or multivalent refers to the number of valency of the β-1,2-linked mannooligosaccharides bonded via linkers B to a central core unit or carrier in a compound of the invention. The compounds are advantageously oligovalent, hence the number of valency in a β-1,2-linked mannooligosaccharide compound is preferably from 3 to 5, in other words, trivalent, tetravalent and pentavalent compounds are preferred. However, if arranged as an assembly comprising two or more immunostimulatory β-1,2-linked mannooligosaccharide compounds, comprising two or more central core or carrier units respectively, said assembly may form a multivalent structure.

In one preferred embodiment of the invention, the immunostimulatory compounds according to the invention are trivalent β-1,2-linked mannooligosaccharide compounds (i.e. m is 3). Trivalent β-1,2-linked mannooligosaccharide compounds mean oligovalent carbohydrate molecules where three (m=3) β-1,2-linked mannooligosaccharides are coupled to a central core unit or a carrier via linker group (B). When acetylated, the trivalent disaccharide is more soluble in aqueous environment than the corresponding analogues with higher valency.

According to one embodiment of the invention, the immunostimulatory compound of the invention consists of a trivalent carbohydrate derivative where three β-1,2-linked mannodisaccharides are linked to a central core unit. Preferably, trivalent β-1,2-linked mannodisaccharide is in accordance with formula (II)

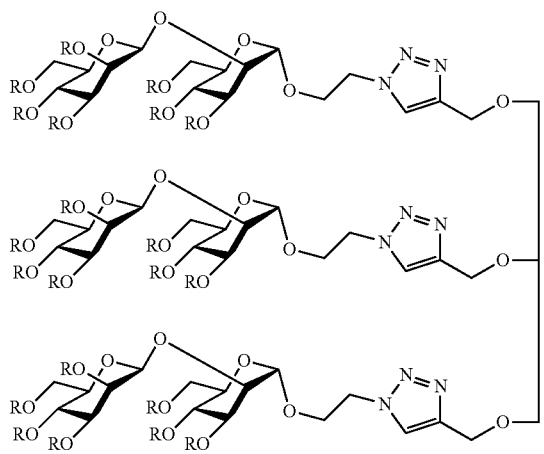

(II)

wherein each R is independently selected from acetyl (COCH₃), hydrogen (H), trifluoroacetyl (COCF₃) or sulfonate group or other ester group.

According to another embodiment of the invention, trivalent β-1,2-linked mannodisaccharide can be in accordance with formula (III)

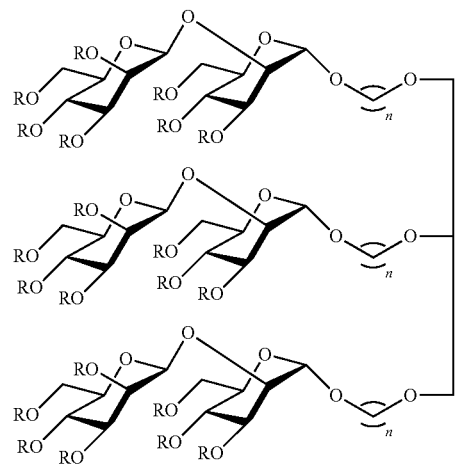

(III)

wherein each R is independently selected form acetyl (COCH₃), hydrogen (H), trifluoroacetyl (COCF₃) or sulfonate group or other ester group, and n is typically 4 or 6.

Triazole moieties (a linker group of compound of formula II) can for example be replaced by simple carbon chains (a linker group of compound of formula III) containing for example four or six carbon atoms providing similar chain length as a triazole-bridge in the trivalent molecule.

The synthesis of the trivalent immunostimulatory compounds according to the invention is preferably based on the use of the click chemistry protocol.

According to an embodiment of this invention, all Rs in said compound represented by formula I are the same. According to a preferred embodiment, the immunostimulatory compound according to the invention is in accordance with formula (II) and all Rs are acetyls. Hence, the immunostimulatory compound according to invention is preferably 1,2,3-tris[1-[(2,3,4,6-tetra-O-acetyl-β-D-mannopyranosyl)-(1→2)-(3,4,6-tri-O-acetyl-α-D-mannopyranosyloxyethyl)]-4-[methyl-1-oxy]triazolyl]propane as is shown in formula (IV):

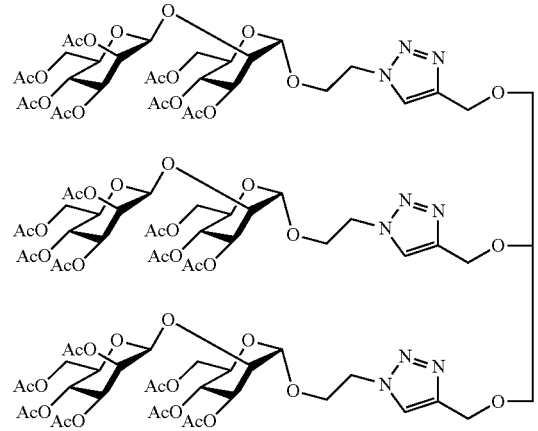

(IV)

The trivalent molecule of formula (IV) incorporating a linker group comprising a triazole moiety and a propane derivative as core unit, into which three 3-1,2-linked mannodisaccharide moieties have been coupled was found as the most active substance for the production of cytokines IFN-γ and IL-10 for potential regulation of immune system. The molecule, which has a decreasing number of valency compared to the compound of the invention, does not have immunostimulating activity and an increasing number of valency compromises certain benefits achieved due to small size. When studying for example acetylated immune-stimulatory compounds of the invention, the increase in the size of molecule i.e. from trivalent to pentavalent causes solubility problem in water. Thus, the trivalent molecule according to the invention is found to be the most attractive immune-stimulatory compound when operating in aqueous conditions. However, in different matrix or conditions, e.g. in lipophilic, other valency may provide better properties over trivalent molecule.

The functional group R is selected from the group of acetyl ($COCH_3$), hydrogen (H), trifluoroacetyl ($COCF_3$) or sulfonate group such as $NaSO_3^-$ or some other functional group. In some applications or embodiments of the present invention, there may be a need to adjust the properties of immunostimulatory compound e.g. with regard to administration to a subject in need thereto, uptake in metabolism, formulation of the pharmaceutical product, stability issues, etc. Selecting functional group R to conform to these requirements is routine knowledge to a man skilled in the art.

The present invention also provides the immunostimulatory compound according to the invention for use as a medicament. One embodiment of the present invention provides the immunostimulatory compound according to the invention for use as an adjuvant of a vaccine.

The present invention also provides an immunostimulatory compound according to the invention or any combination thereof for use in treating a condition which can be prevented or treated by inducing a Treg- and/or Th1-type, and/or inhibiting a Th2-type immune response.

Treg- and/or Th1-type immune response is induced by induction of IFN-γ production in T cells, and/or inhibition or suppression of the function of Th2-type T cells, mast cells, eosinophil granulocytes and/or basophil granulocytes. Th2-type immune response is inhibited by induction of IL-10 production in T-cells and/or inhibition or suppression of the function of Th2-type T cells, mast cells, eosinophil granulocytes and/or basophil granulocytes. The inhibition of Th2-type immune response is also based on the suppression of allergen-induced IL-5 production.

The invention also provides the immunostimulatory compound according to the invention for use in treatment of type I immediate atopic allergy. In preferred embodiments, the type I immediate atopic allergy is selected from the group of atopic eczema/dermatitis syndrome (AEDS), allergic asthma, allergic rhinitis, allergic urticaria, food allergy, venom allergy, and allergic rhinoconjunctvitis. In further embodiments, the invention provides the immunostimulatory compound of the invention for use in treatment of infectious diseases.

The present invention is also directed to an immunostimulatory composition comprising at least one of the immunostimulatory compounds according to the invention or mixtures thereof, and a pharmaceutically acceptable carrier.

The present invention also provides use of the immunostimulatory compound according to the invention and/or any combination thereof as a food additive.

The present invention also provides a method for inducing of Treg- and/or Th1-type immune response comprising administering to a subject the composition of the invention in an amount effective to induce a Treg- and/or Th1-type immune response, and a method for inhibition of Th2-type immune response comprising administering to a subject the composition of the invention or the food of the invention in an amount effective to partially or completely inhibit development of Th2-type immune response.

DETAILED DESCRIPTION OF THE INVENTION

Figure 1:
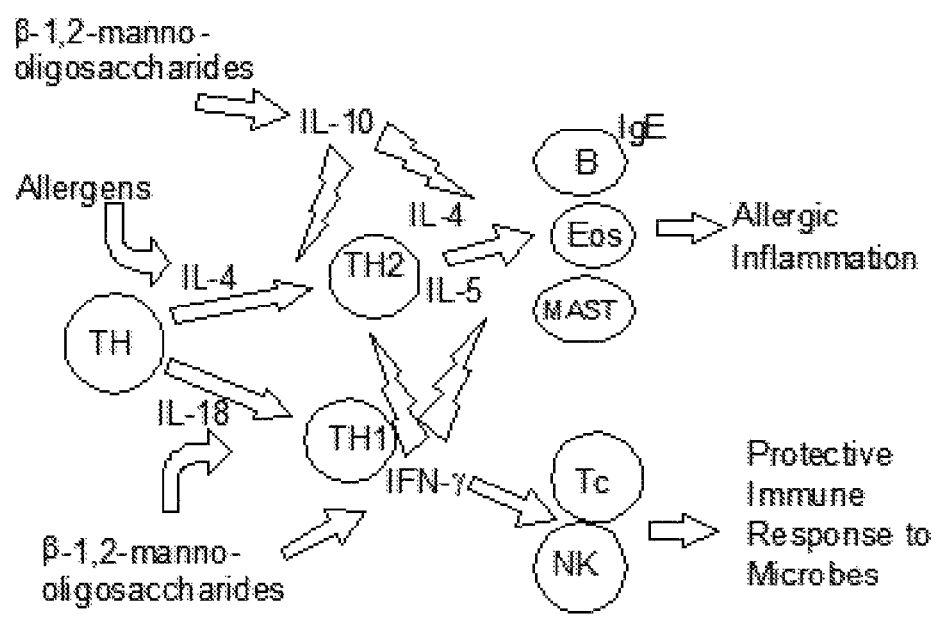
FIG. 1 illustrates β-1,2-linked mannooligosaccharide-mediated modulation of Th-immune response.

The mechanism provided by immunostimulatory oligo- or multivalent β-1,2-linked mannooligosaccharide compounds of the present invention is believed to be carbohydrate mediated modulation of Th-immune response as presented in FIG. 1. Essential components of said carbohydrate moiety are β-1,2-linked mannooligosaccharides. In the context of this application the term β-1,2-mannooligosaccharide refers to carbohydrate moieties consisting of two to eight mannopyranose moieties. The oligovalent compound may also incorporate mannose or other monosaccharide moieties.

Allergic inflammation is characterized by IgE antibody production, mast cell degranulation and eosinofilic inflammation. These responses are mediated by allergen-specific Th2-type immune cells that secrete cytokines such as IL-4 and IL-5. The Th1 cells that secrete cytokines, including IFN-γ are involved in suppression of allergen-induced Th2-type immune responses. The regulatory cytokine IL-10 is also important in down-regulation of Th2-type immune responses. Based on the experiments described in examples, the discovery that trivalent β-1,2-linked mannodisaccharides according to the invention stimulate the IFN-γ and IL-10 in human white blood cells suggests these cytokines have a role in β-1,2-mannooligosaccharide-mediated suppression of Th2 cell response, and thus allergic inflammation.

The present invention describes synthetic immunostimulatory oligo- or multivalent β-1,2-linked mannooligosaccharide compounds and the use of such molecules or their prodrugs for modulation of above described Th-mediated immune responses and in the manufacture of a medicament, pharmaceutical and nutritional preparation for prevention or treatment of type I atopic allergies and infectious diseases in a subject.

When discussing immunology, it is worth noting that immunogens are used to stimulate the specific immune response against the immunogen. Immunostimulants, however, are used to stimulate a non-specific activation of the immune system in order to enhance a specific immune response against a co-administrated immunogen.

The term immunostimulant or immunostimulatory compound refers to a biologically active substance, whose activities affect or play a role in the functioning of the host subject's immune system by stimulating T helper type 1 and regulatory type T cell responses. The term subject refers to a mammal, including human. Immunostimulant induces non-specific activation of the immune system. Immunostimulants are used among other applications also as vaccine adjuvants to enhance a specific humoral or cellular immune response against a vaccine immunogen co-administrated together with immunostimulatory compound.

Hence, immunostimulatory compound according to the invention is also suitable for use as an adjuvant of the vaccines. Immunostimulatory compound according to the invention or the mixtures thereof are added to vaccines as adjuvant to stimulate the immune system's response to the target antigen, but do not in themselves confer immunity. Especially, compounds according to the invention are suitable for use as adjuvants in injections of desensitization. Also, the compounds of the invention can be used as an adjuvant in vaccines against infectious diseases. Preferably, when used as an adjuvant, the immunostimulatory compound according to the invention may be coadministered with the main component, the immunogen in question. However, the immunostimulatory compound according to the invention may optionally be engineered to be bonded or further linked to said immunogen or to another component of the vaccine composition.

The invention also encompasses a method for inducing a Treg- and/or Th1-type immune response. The method involves administrating to a subject composition according to the invention in an amount effective to induce the synthesis of Treg- and/or Th1-type cytokines. In preferred embodiments, the method involves, but is not limited to, the induction of IFN-γ synthesis in T cells.

The invention further involves a method for inhibiting a Th2-type immune response. The method involves administrating to a subject the composition according to the invention in an amount effective to partially or completely inhibit the development of Th2-type immune response to an allergen. In preferred embodiments, the mechanisms of inhibition include, but are not limited to, induction of IL-10 production in T cells. The method can also involve suppression of Th2-type immune response by inhibition or suppression of the function of Th2-type T cells, mast cells and eosinophil and basophil granulocytes.

More specifically immunostimulatory compound according to the present invention is preferable for use wherein a Treg- and/or Th1-type immune response is induced by
 a) induction of IFN-γ production in T cells, and/or
 b) inhibition or suppression of the function of Th2-type T cells, mast cells, eosinophil granulocytes and/or basophil granulocytes.

Furthermore, an immunostimulatory compound according to the present invention is preferred for use wherein a Th2-type immune response is inhibited by
 a) induction of IL-10 production in T-cells and/or
 b) inhibition or suppression of the function of Th2-type T cells, mast cells, eosinophil granulocytes and/or basophil granulocytes.

The present invention also provides a method for modulating a Th-mediated immune response. Preferably, the immune response stimulated according to the invention is biased toward the Th1-type response and away from the Th2-type response. In one aspect, the method involves administrating to a subject said composition in an amount effective to stimulate the production of Th1-type cytokines. In preferred embodiments, the method involves, but is not limited to, the induction of IFN-γ synthesis in T cells. In other aspect, the method involves administrating to a subject said composition in an amount effective to partially or completely inhibit the development of Th2-type immune response to allergen. In preferred embodiments, the mechanisms of inhibition include, but are not limited to, induction of IL-10 production in T cells. The method can also involve suppression of Th2-type immune response by inhibition or suppression of the function of Th2-type T cells, mast cells and eosinophil and basophil granulocytes.

The invention further relates to the use of a composition according to the invention for the manufacture of a medicament, pharmaceutical, or nutritional preparation for prevention or treatment of type I immediate atopic allergies. In preferred embodiments, the type I immediate atopic allergy is selected from the group consisting of atopic eczema/dermatitis syndrome (AEDS), allergic asthma, allergic rhinitis, allergic urticaria, food allergy, venom allergy, and allergic rhinoconjunctivitis. In further embodiments, the compound of the invention can be used for prevention and treatment of infectious diseases. The term prevent, prevention or preventing used herein refers to inhibiting completely or partially the development of the disorder in a subject that has, or is at high risk of developing, said disorder. The term treat, treatment or treating is defined as administering to a subject an amount of said compound or composition effective to prevent the onset of, alleviate the symptoms of, or stop the progression of the disorder. The term effective amount used herein refers to an amount effective, at dosages and for periods of time necessary, to achieve the desired therapeutic result. The therapeutically effective amount typically varies from about 1 μg to several grams depending on the composition and especially the mode of administration. E.g. the typical amount for parenteral administration of trivalent β-1,2-linked mannodisaccharide according to the invention, is from 1 μg to 100 μg, preferably 2 μg to 30 μg, most preferably 3 μg to 10 μg, and for oral administration the typically amount can be much higher from a few mg up to several grams. If a prodrug is administered, the effective amount depends on how much immunostimulatory β-1,2-linked mannooligosaccharide compound, e.g. trivalent β-1,2-linked mannodisaccharide, it can result in and how much of it is actually released.

In further embodiments, the medicament or pharmaceutical preparation of the invention may be administered to a subject by any route known in the art, including enteral, mucosal, parenteral and topical routes. The enteral routes include oral and any route involving absorption from the gastrointestinal tract. The mucosal routes include, but are not restricted to, oral, nasal, sublingual, buccal, pulmonary, transdermal and ocular routes. The parenteral routes include, but are not restricted to, intravenous, intradermal, intramuscular, and subcutaneous routes.

In some embodiments, the composition of the invention is used in conjugation with a pharmaceutically acceptable carrier. An immunostimulatory composition according to the invention typically includes at least one of the immunostimulatory compounds according to the invention or mixtures thereof, and a pharmaceutically acceptable carrier. The term pharmaceutically acceptable carrier refers to a carrier substance with which the active ingredient is combined to facilitate the application to a subject and that is physiologically acceptable to the recipient. The pharmaceutically acceptable carrier can be selected from the group consisting of, but not restricted to, transdermal carriers, transmucosal carriers, oral carriers, parenteral carriers, carriers for depot formulations, and carriers for extended release formulations.

Immunostimulatory compound of the present invention may be encapsulated, incorporated or dissolved into a matrix, which can provide extended release systemic delivery. It may optionally be adapted for use to provide extended delivery within localized tissue region, for example within site of allergic reaction, infection site or vaccination site. This sustained release or controlled release is intended to refer to encompass release of that occurs as the result of bio-degradation in vivo of the depot or component thereof, or as the result of the metabolic transformation or dissolution releasing said immunostimulatory compound. For example in subcutaneous injections, when immunostimulatory compound is used as an adjuvant together with the allergen, it might in itself function as a depot that will leak out to the blood/surrounding tissue over time.

Alternatively, the immunostimulatory compound of the present invention may be conjugated from the core unit or a carrier directly to a lipid group which can then provide a depot preparation. These lipid modified or lipidated immunostimulatory compounds may be used for formation of suspensions, incorporation into emulsions, lipid membranes, lipid vesicles, liposomes and the like.

In further embodiments, the pharmaceutical composition of the invention may include another therapeutic compound. The term therapeutic compound used herein is preferentially an allergy medicament, an asthma medicament or antimicrobial agent. In other embodiments, the pharmaceutical composition of the invention comprises an antigen. The term antigen broadly includes any type of molecule (e.g. protein, peptide, polysaccharide, glycoprotein, nucleic acid, or combination thereof) that is recognized by a host immune system and is capable of eliciting a specific immune response. In some embodiments the antigen is an allergen preparation for specific allergen immunotherapy (allergen vaccination or sublingual immunotherapy). The term allergen used herein refers to a substance that can induce an allergic or asthmatic response in a susceptible subject, and includes but is not limited to pollens, insect venoms, animal dander, fungal spores and house dust mite. The term specific allergen immunotherapy, which is also known as allergen immunotherapy, hyposensitization therapy or immunologic desensitization, refers to treatment of a subject with allergic disorder by administrating gradually increasing amounts of allergen by any of the known routes to induce immunologic tolerance to the allergen to prevent further allergic reactions. Hence, the composition of the invention can also comprise an allergen preparation for specific allergen immunotherapy; and/or an additional allergy or asthma medicament.

Alternatively, the pharmaceutical composition of the invention further comprises a microbe-specific antigen preparation for vaccination or immunization against infectious diseases and/or an antimicrobial agent. The term infectious disease refers to a disease arising from the presence of foreign microorganisms or infectious pathogens in the body. The term infectious pathogens, i.e. microbes, refers to viruses, bacteria and parasites. As such, the term infectious pathogens also includes normal flora, which is not desirable. In one aspect, the combined administration of the pharmaceutical composition of the invention and microbial antigen is useful for stimulating enhanced immune response to malignant cells and pathogens. The term microbial antigens used herein include intact microorganisms, as well as natural isolates and fragments or derivates thereof, and also synthetic compounds, which are identical to or similar to natural microbial antigens. In yet other embodiments, the pharmaceutical composition of the invention comprises antibodies or antibody fragments which specifically bind or recognize microbial antigens.

In yet other embodiments, the compound of the invention is used as a food additive. The compound of the invention can also be formulated to a nutritional preparation. The nutritional preparation is preferentially enterally administrable, e.g. powder, tablet, capsule, a liquid concentrate, solid product, or ready-to drink beverage. Alternatively, the nutritional preparation of the embodiment is combined with a matrix suitable as an additive of usual food products. In other embodiments, the nutritional preparation of the invention is used for enrichment of infant formulas and other functional food products. A further embodiment comprising the composition of the invention could be a chewing gum.

Synthesis of β-1,2-Linked Mannooligosaccharide Compounds According to the Invention The syntheses and development in this field has been driven by the need of potent carbohydrate inhibitors for understanding the different factors involved in protein-carbohydrate interactions. Features such as structure, shape, size, geometry, and valence have proved to be determinant factors in influencing the generally weak binding properties of carbohydrate ligands. To overcome these weak binding interactions, multivalent neoglycoconjugates ranging from clusters and oligomers, to macromolecular polydispersed systems such as glycopolymers and glycol-dendrimers have been generated to provide antiadhesins of higher affinity. A large number of these multivalent carbohydrate ligands demonstrated powerful inhibitory properties when tested against their specific animal or plant lectins. In the area of multivalency, the development of multivalent carbohydrates of varying size as effectors of biological processes through clustering of receptors has been a topic of interest. Generally, carbohydrates involved in the binding are connected together through linkers. The Huisgen 1,3-dipolar cycloaddition between azides and alkynes to afford triazoles is probably the most powerful"click" reaction for such linkages. In the field of carbohydrate chemistry, click chemistry has been used for the synthesis of glycoconjugates and carbohydrate macrocycles in which a sugar possessing an azido function is grafted onto a saccharide a peptide, or a polymeric chain.

Some approaches are currently available to be applied for synthesizing β-1,2-linked mannooligosaccharide compounds of the invention. One especially suitable is so called Click chemistry protocol (Ballell et al., 2006; Pérez-Balderas et al., 2005).

Figure 2:
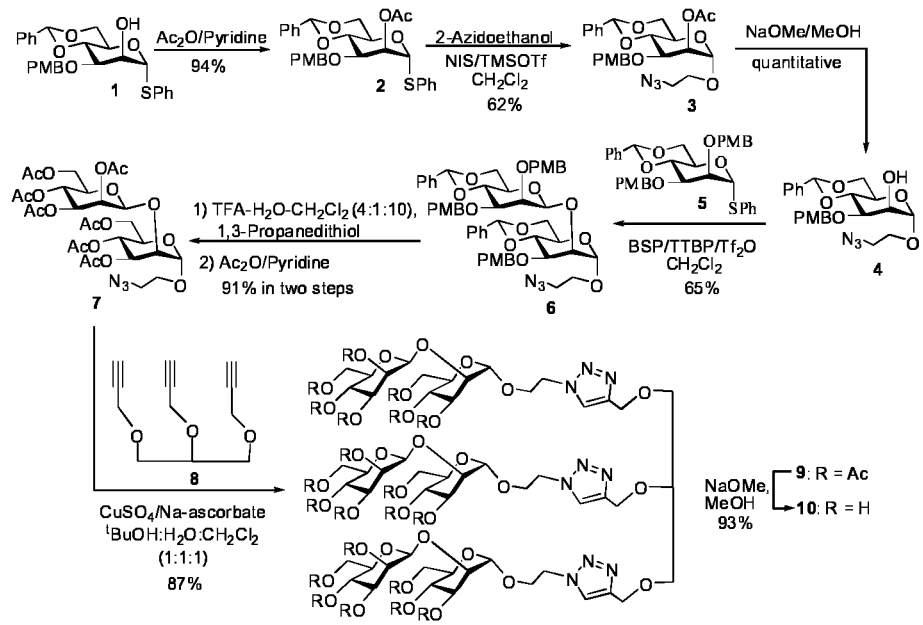
FIG. 2 illustrates synthesis of β-1,2-linked mannodisaccharide containing trivalent compounds according to formula (II) of the invention, and more specifically compound (IV)

Said Click chemistry protocol has now been used for synthesizing trivalent molecules based on β-1,2-linked mannodisaccharide according to the invention. Cu(I)-mediated click reaction between 2-azidoethyl glycoside of β-1,2-linked mannodisaccharide and glycerol based tri-O-propargyl compound furnished the desired trivalent molecules in good yield.

β-1,2-linked mannodisaccharide based trivalent compounds 9 (acetyl form) and 10 (hydroxyl form) were prepared from partially protected thioglycoside 1 (Crich et al., 2006) in minimum number of steps, as is shown in FIG. 2. Compound 9 is congruent with the compound of formula (IV) of the invention. An acetyl group was introduced (for anchimeric assistance during α-selective glycosyation) at the C-2-position of 1 to give glycosyl donor 2. Glycosylation between donor 2 and 2-azidoethanol (Pfaendler et al., 1996) in the presence of N-iodosuccinimide-TMSOTf (Ohlsson et al., 2000) afforded 1,2-trans product 3 in 62% yield. Zemplén deacetylation of compound 3 gave glycosyl acceptor 4 (Alpe et al., 2003) in quantitative yield.

Using BSP/Tf$_2$O-mediated β-selective glycosylation (Crich et al., 2001) of compound 4 and glycosyl donor 5 (Crich et al., 2002) afforded disaccharide 6 in 65% yield. The presence of β-linkage was confirmed by the $^1J_{CH}$ coupling constant value 157.0 Hz of the anomeric carbon at δ 100.8 (Bocks et al., 1974), whereas the presence of α-linkage was confirmed by $^1J_{CH}$ coupling constant value 168.2 Hz of the anomeric carbon at δ 98.6 (Crich et al., 2000). TFA-mediated deprotection (Codée et al., 2005) of all the ether groups of glycoside 6 followed by conventional acetylation gave compound 7 in 91% yield over two steps. Application of robust click coupling between 2-azidoethyl glycoside 7 and tri-O-propargyl glycerol 8 (Mourer et al., 2008) furnished acetylated trivalent compound 9 in 87% yield, which upon Zemplén deacetylation afforded fully deprotected trivalent compound 10 in 93% yield (FIG. 2).

Figure 3:
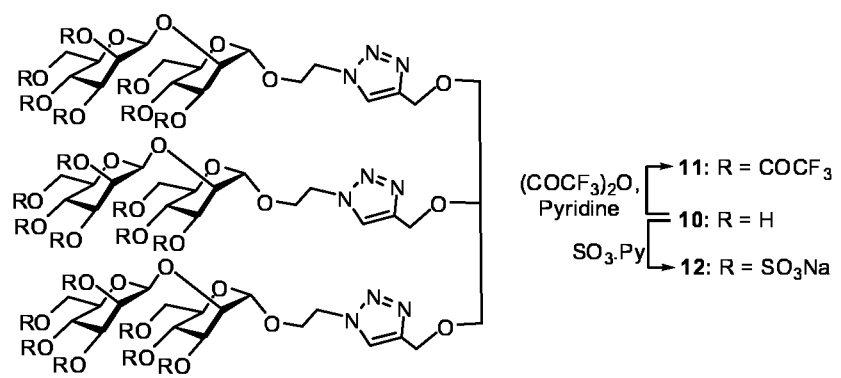
FIG. 3 illustrates functional group modification of β-1,2-linked mannodisaccharide containing trivalent compound.
Figure 4:
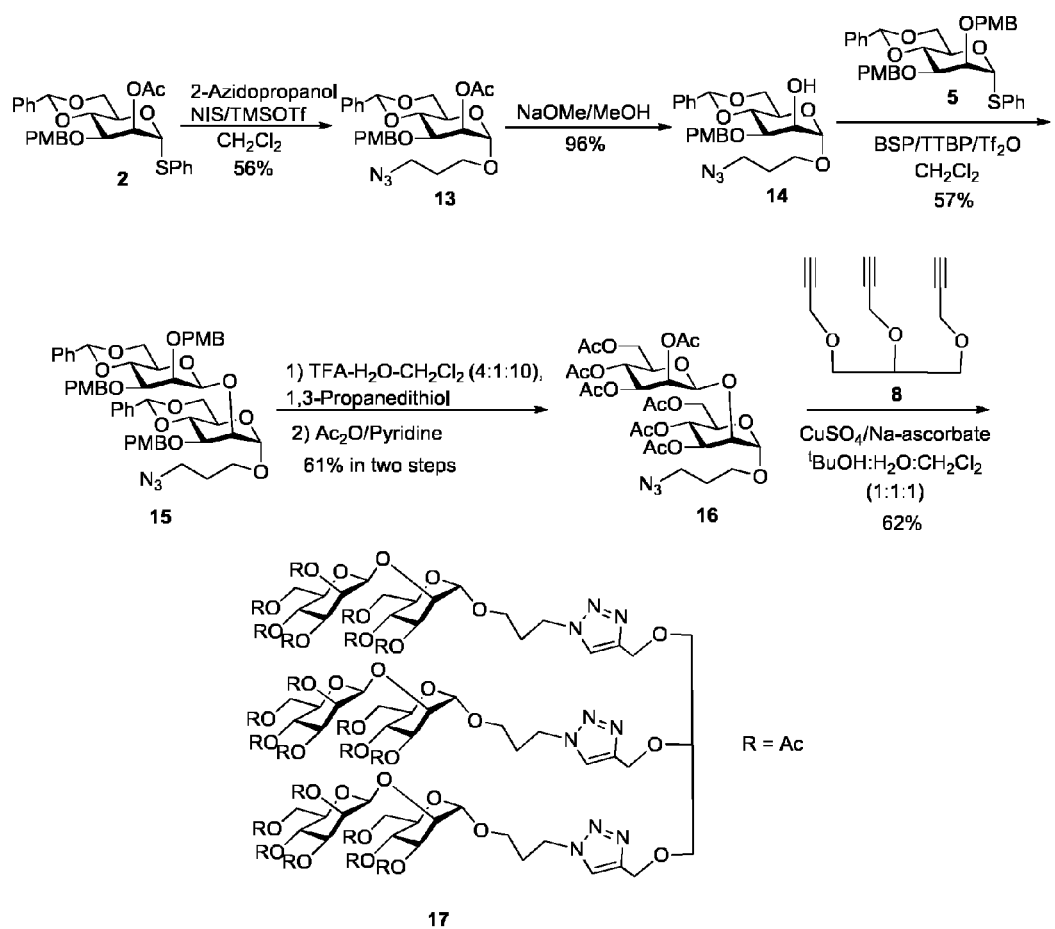
FIG. 4 illustrates the synthesis of the an active a β-1,2-linked mannodisaccharide compound with one —$CH_2$— added to the triazole containing linker of compound (IV)

Functional Group Modification of β-1,2-Linked Trivalent Mannooligosaccharide Compounds According to the Invention The β-1,2-linked mannooligosaccharide compound of the present invention comprises several functional groups represented by R in formulas (I, II, III) and FIGS. 2, 3 and 4. They can be converted into mannooligosaccharide derivatives thereof by routine treatment, wherein at least one hydrogen of the ring hydroxyl groups is replaced by another chemical moiety. In one embodiment, an acetyl or $C_2$-$C_6$ acyl group or a protecting group such as a benzyl or chlorobenzyl group is used to form a mannopyranose derivative. Using protecting groups or other substituents in these positions may be beneficial during the synthesis of compounds or alternatively the formulation or administration of a medicament comprising the β-1,2-linked mannooligosaccharide compounds of the present invention. When converting functional groups R to derivatives thereof, all groups represented by R may be converted in the same reaction step or alternatively the conversion may take place to R groups in selected positions resulting in a compound having variable substituents. However, preferably, all the R groups are reacted to represent the same substituent. The acetyl and acyl derivatives can be hydrolyzed in vivo to form a mannopyranose conjugate.

This is illustrated more specifically in FIG. 3, showing how trivalent mannoside 10 can be derivatized to other functional groups. Upon reaction with trifluoroacetic anhydride/pyridine, trivalent 10 can be transformed to 11, whereas treatment with SO$_3$.Py/pyridine (de Paz et al., 2005) hydroxyl groups of 10 can be converted to more hydrophilic sulfate groups thus forming trivalent 12 as is shown in FIG. 3. The derivatization, if desired, can be removed e.g. prior to administration giving again compound 10.

Structural Modification on the Linker Part of β-1,2-Linked Mannooligosaccharide Compounds According to the Invention The inventors have found and shown experimentally that the β-1,2-linked mannooligosaccharide compounds provide excellent results even when different linker structures have been employed. The linker may, for example, comprise either a triazole moiety or a derivative thereof.

Copper mediated azide-alkyne cycloaddition (click chemistry) reaction produces triazole moiety at the point of attachment. These triazole moieties can enhance the bioactivities of a molecule by association with the target through hydrogen bonding. Thus it may not be only a passive linker. In order to realize their effect these triazole moieties can be replaced by simple carbon chain with similar spacer length. A mannodisaccharide-containing trivalent molecule having a simple carbon chain can be synthesized with more or less similar fashion.

To synthesize β-1,2-linked mannodisaccharide-containing trivalent compounds, thioglycoside can be used as glycosyl donor for introduction of initial α-linkage. NIS/TMSOTf-mediated α-selective glycosylation of said thioglycoside with allyl alcohol could furnish an allyl glycoside. Zemplén deacetylation of this allyl glycoside could give a glycosyl acceptor, which upon BSP/Tf$_2$O-mediated β-selective glycosylation with glycosyl donor could furnish a disaccharide. Hydroboration with 9-BBN followed by oxidation with H$_2$O$_2$/NaOH could convert double bond of said disaccharide to primary alcohol thus forming a 2-hydroxyethyl glycoside (Soderquist et al., 1980). Upon treatment with CBr$_4$/PPh$_3$, a hydroxyl group can be transformed to a bromo group to furnish an intermediate according to Bentz et al., 2006 and Matsuda et al., 2006).

With acetylide anion it could further form a carbon-carbon bond to furnish trivalent compound, which upon catalytic hydrogenation/hydrogenolysis in the presence of hydrogen over 10% Pd—C could afford fully deprotected and saturated β-1,2-linked mannodisaccharide-containing trivalent compound. Conventional acetylation thereof could furnish an acetylated derivative. Additionally, treatment with SO$_3$.Py/pyridine could furnish sulphated derivative.

EXAMPLES

Experimental Synthesis of β-1,2-Linked Trivalent Mannooligosaccharide Compounds

Experimental synthesis of β-linked trivalent mannosides has been described in the following by using the reference numbers of FIG. 2.

Phenyl 2-O-acetyl-4,6-O-benzylidene-3-O-p-methoxybenzyl-1-thio-α-D-mannopyranoside (2)

To a solution of compound 1 (1.85 g, 3.85 mmol) in pyridine (10 mL) was added acetic anhydride (5 mL) and the mixture was stirred at room temperature for 4 h. The solvent was evaporated followed by co-evaporation with toluene (3×10 mL). The crude reaction mixture was purified over SiO$_2$ (hexane/EtOAc; 5:1) to afford pure compound 2 (1.9 g, 94%) as a colorless foam. ESI-HRMS, Calcd. for C$_{29}$H$_{30}$O$_7$SNa [M+Na]$^+$: 545.1610. found: 545.1622.

2-Azidoethyl 2-O-acetyl-4,6-O-benzylidene-3-O-p-methoxybenzyl-α-D-mannopyranoside (3)

To a solution of compound 2 (1.5 g, 2.87 mmol) and 2-azidoethanol (300 mg, 3.44 mmol) in CH$_2$Cl$_2$ (15 mL) was added 4 Å molecular sieves (1.5 g) and the mixture was stirred at room temperature for 30 min under argon atmosphere. NIS (775 mg, 3.44 mmol) was added and the reaction mixture was cooled to −40° C. followed by the addition of TMSOTf (38 mg, 31 µl, 0.17 mmol). The reaction mixture was stirred for 2 h at the same temperature and quenched with Et$_3$N (100 µl). The reaction mixture was filtered over a pad of celite and washed with CH$_2$Cl$_2$ (40 mL). The combined organic layer was washed with water (30 mL), satd. aq. NaHCO$_3$ (2×30 mL) and brine solution (2×30 mL) respectively. The organic layer was then dried (Na$_2$SO$_4$), concentrated and purified over SiO$_2$ (hexane/EtOAc; 7:2) to afford pure 3 (890 mg, 62%) as a colorless foam. ESI-HRMS, Calcd. for $C_{25}H_{29}N_3O_8Na$ [M+Na]$^+$: 522.1852. found: 522.1839.

2-Azidoethyl 4,6-O-benzylidene-3-O-p-methoxybenzyl-α-D-mannopyranoside (4)

To a solution of compound 3 (780 mg, 0.05 mmol) in MeOH (20 mL) was added sodium methoxide (0.1 M in MeOH, 600 µL) and the mixture was stirred at room temperature for 2 h. Dowex® 50WX8-100 (H$^+$) was added to neutralize. The reaction mixture was filtered and washed with methanol (3×10 mL). The combined organic layer was evaporated to dryness under reduced pressure to furnish compound 4 (690 mg, quantitative) as a colorless oil. Characterization data for 4 are in accordance with that reported in the literature (Alpe et al., 2003).

2-Azidoethyl (4,6-O-benzylidene-2,3-di-O-p-methoxybenzyl-β-D-mannopyranosyl)-(1→2)-4,6-O-benzylidene-3-O-p-methoxybenzyl-α-D-mannopyranoside (6)

To a solution of glycosyl donor 5 (1.5 g, 2.49 mmol) in $CH_2Cl_2$ (20 mL) was added 4 Å molecular sieves (2 g) and the mixture was stirred for 30 min at room temperature under argon atmosphere. BSP (630 mg, 2.99 mmol) and TTBP (930 mg, 3.74 mmol) were added at −60° C. followed by the addition of Tf$_2$O (920 mg, 550 µl, 3.24 mmol) and stirring under the same conditions for 30 min. Compound 4 (950 mg, 2.08 mmol) in $CH_2Cl_2$ (10 mL) was added to the reaction mixture at −78° C. and stirred for 2 h at this temperature before quenching with Et$_3$N (1 mL). The reaction mixture was then filtered through a pad of celite followed by washing with $CH_2Cl_2$ (60 mL). The combined organic layer was washed with water (2×30 mL), brine (20 mL), dried (Na$_2$SO$_4$), concentrated and purified over SiO$_2$ (hexane/EtOAc; 5:2) to afford the β-isomer 6 (1.27 g, 65%) as a colorless foam. ESI-HRMS, Calcd. for $C_{52}H_{57}N_3O_{14}Na$ [M+Na]$^+$: 970.3739. found: 970.3717.

2-Azidoethyl (2,3,4,6-tetra-O-acetyl-β-D-mannopyranosyl)-(1→2)-3,4,6-tri-O-acetyl-α-D-mannopyranoside (7)

To a stirred solution of compound 6 (1.0 g, 1.05 mmol) and 1,3-propanedithiol (915 mg, 850 µL, 8.44 mmol) in $CH_2Cl_2$ (10 mL) was added TFA-H$_2$O (5 mL, 4:1) at 0° C. and stirring was continued for 2 h at room temperature. The reaction mixture was diluted with water (15 mL) and washed with $CH_2Cl_2$ (4×15 mL) to remove all nonpolar organic materials. The aqueous layer was evaporated followed by co-evaporation with toluene (4×20 mL) under reduced pressure. The crude product was then dissolved in pyridine (20 mL) followed by the addition of Ac$_2$O at 0° C. where after the reaction mixture was stirred at room temperature for 20 h. Solvents were evaporated under reduced pressure followed by co-evaporation with toluene (3×20 mL). The crude mixture was then purified over SiO$_2$ (hexane/EtOAc; 1:1) to afford the acetylated product 7 (675 mg, 91%) as a white powder. ESI-HRMS, Calcd. for $C_{28}H_{39}N_3O_{18}Na$ [M+Na]$^+$: 728.2127. found: 728.2112.

1,2,3-Tris[1-[(2,3,4,6-tetra-O-acetyl-β-D-mannopyranosyl)-(1→2)-(3,4,6-tri-O-acetyl-α-D-mannopyranosyloxyethyl)]-4-[methyl-1-oxy]triazolyl]propane (9), i.e. compound according to the formula (IV) of the invention To a solution of 2-azidoethyl glycoside 7 (300 mg, 0.43 mmol) and 8 (26.6 mg, 0.13 mmol) in $^t$BuOH:H$_2$O:CH$_2$Cl$_2$ (6 mL, 1:1:1, v/v/v), copper sulfate (6.2 mg, 0.04 mmol) and sodium ascorbate (15.3 mg, 0.08 mmol) were added respectively and heated at 55° C. for 12 h. Satd. NH$_4$Cl and water (20 mL, 1:1) was poured into the solution followed by extraction with $CH_2Cl_2$ (3×20 mL). The organic layer was dried (Na$_2$SO$_4$), filtered, concentrated and purified over SiO$_2$ (4% MeOH in $CH_2Cl_2$) to afford the pure title compound 9 (260 mg, 87%) as a colorless solid. R$_f$: 0.45 (7% MeOH in $CH_2Cl_2$); $[α]_D^{25}$ −67.5° (c 1, CHCl$_3$); $^1$H NMR (600.13 MHz, CDCl$_3$) δ 7.80 (s, 1H), 7.73 (s, 1H), 7.72 (s, 1H), 5.48-5.46 (m, 3H), 5.25-5.21 (m, 6H), 5.04-5.00 (m, 3H), 4.91-4.87 (m, 3H), 4.81-4.77 (m, 5H), 4.70-4.69 (m, 3H), 4.67-4.55 (m, 10H), 4.34-4.30 (m, 3H), 4.28-4.27 (m, 3H), 4.20-4.16 (m, 3H), 4.14-4.09 (m, 3H), 4.02-3.99 (m, 6H), 3.93-3.90 (m, 3H), 3.82 (quintet, J=5.2 Hz, 1H), 3.69-3.54 (m, 10H), 2.23 (br s, 9H), 2.12 (br s, 9H), 2.09 (br s, 9H), 2.04 (br s, 9H), 2.03 (br s, 6H), 2.02 (br s, 9H), 2.01 (s, 3H), 2.00 (brs, 9H); $^{13}$C NMR (150.9 MHz, CDCl$_3$) δ 170.8 (3C), 170.6, 170.5 (2C), 170.3, 170.2 (4C), 170.1, 169.9, 169.8 (2C), 169.6 (3C), 169.2, 169.1 (2C), 145.5, 145.0, 144.9, 123.8, 123.7 (2C), 97.4 (3C), 96.2 (3C), 77.1, 72.1 (2C), 72.0, 71.9, 71.8 (2C), 70.6, 70.5 (2C), 70.0 (4C), 69.9, 68.9 (2C), 68.8, 68.4 (3C), 66.0 (3C), 65.9 (3C), 64.7 (3C), 64.4 (2C), 63.5, 62.3 (3C), 61.6, 61.5 (2C), 49.7 (2C), 49.6, 20.7 (6C), 20.6 (6C), 20.5 (6C), 20.4 (3C); MALDI-TOF-MS, Calcd. for $C_{96}H_{131}N_9O_{57}Na$ [M+Na]$^+$: 2344.752. found: 2344.768.

1,2,3-tris[1-(β-D-mannopyranosyl)-(1→2)-(α-D-mannopyranosyloxyethyl)]-4-[methyl-1-oxy]triazolyl] propane (10)

To a solution of compound 9 (47 mg, 0.02 mmol) in MeOH (3 mL) was added sodium methoxide (0.1 M in MeOH, 100 µL) and the mixture was stirred at room temperature for 2 h. Dowex® 50WX8-100 (H$^+$) was added to neutralize. The reaction mixture was filtered and washed with methanol (3×20 mL). The combined organic layer was evaporated to dryness under reduced pressure to afford pure 10 (27 mg, 93%) as a white foam. $[α]_D^{25}$ −2.0° (c 1, H$_2$O); $^1$H NMR (600.13 MHz, D$_2$O) δ 8.09 (br s, 2H), 8.08 (s, 1H), 4.92-4.90 (m, 3H), 4.74 (br s, 2H), 4.70-4.64 (m, 13H), 4.14-4.09 (m, 3H), 4.08-4.06 (m, 3H), 4.00 (d, J=3.2 Hz, 3H), 3.97-3.87 (m, 8H), 3.74-3.61 (m, 21H), 3.55 (t, J=9.7 Hz, 3H), 3.36-3.32 (m, 3H), 3.02-2.98 (m, 3H); $^{13}$C NMR (150.9 MHz, D$_2$O) δ 144.0 (3C), 125.6 (3C), 98.5 (3C), 97.3 (3C), 77.0 (3C), 76.8, 76.3 (3C), 72.8 (2C), 72.7 (3C), 70.7 (3C), 69.8 (3C), 69.0 (2C), 66.6 (4C), 66.5 (3C), 65.5 (3C), 63.3 (2C), 62.1, 60.9 (3C), 60.2 (3C), 50.1 (3C); MALDI-TOF-MS, Calcd. for $C_{54}H_{89}N_9O_{36}Na$ [M+Na]$^+$: 1462.530. found: 1462.548.

The same compound, according to the formula (IV) of the invention, i.e., 1,2,3-tris[1-[(2,3,4,6-tetra-O-acetyl-β-D-mannopyranosyl)-(1→2)-(3,4,6-tri-O-acetyl-α-D-mannopyranosyloxyethyl)]-4-[methyl-1-oxy]triazolyl]propane (9) was produced in larger scale in another experiment. The whole synthesis or characterization of intermediates or end product are not shown here, but said synthesis afforded the pure compound 1,2,3-tris[1-[(2,3,4,6-tetra-O-acetyl-β-D-mannopyranosyl)-(1→2)-(3,4,6-tri-O-acetyl-α-D-mannopyranosyloxyethyl)]-4-[methyl-1-oxy]triazolyl]propane (9) from compounds 7 and 8 in analogous fashion as described above (230 mg, 74%) as colorless solid.

Synthesis of the Analogue of the Immunostimulatory Compound According to the Formula (IV) of the Invention with Elongated Linker

3-Azidopropyl 2-O-acetyl-4,6-O-benzylidene-3-O-p-methoxybenzyl-α-D-mannopyranoside (13)

To a solution of compound 2 (2 g, 3.82 mmol) and 3-azido-1-propanol (464 mg, 4.59 mmol) in $CH_2Cl_2$ (15 mL) was added 4 Å molecular sieves (1.5 g) and the mixture was stirred at room temperature for 30 min under argon atmosphere. NIS (1.03 g, 4.59 mmol) was added and the reaction mixture was cooled to −40° C. followed by the addition of TMSOTf (45 mg, 36 µl, 0.20 mmol). The reaction mixture was stirred for 2 h at the same temperature and quenched with Et₃N (100 µl). The reaction mixture was filtered over a pad of celite and washed with $CH_2Cl_2$ (40 mL). The combined organic layer was washed with water (30 mL), satd. aq. $NaHCO_3$ (2×30 mL) and brine solution (2×30 mL) respectively. The organic layer was then dried ($Na_2SO_4$), concentrated and purified over $SiO_2$ to afford pure 13 (1.09 g, 56%) as colorless foam. Calcd. for $C_{26}H_{31}N_3O_{18}Na$ [M+Na]⁺: 536.2127. found: 536.1952.

3-Azidopropyl 4,6-O-benzylidene-3-O-p-methoxy-benzyl-α-D-mannopyranoside (14)

To a solution of compound 13 (920 mg, 1.79 mmol) in MeOH (20 mL) was added sodium methoxide (0.1 M in MeOH, 600 µL) and the mixture was stirred at room temperature for 4 h. Dowex® 50WX8-100 (H⁺) was added to neutralize. The reaction mixture was filtered and washed with methanol (4×15 mL). The combined organic layer was evaporated to dryness under reduced pressure to furnish compound 14 (827 mg, 96%) as a colorless oil.

3-Azidopropyl (4,6-O-benzylidene-2,3-di-O-p-methoxybenzyl-3-D-mannopyranosyl)-(1→2)-4,6-O-benzylidene-3-O-p-methoxybenzyl-α-D-mannopyranoside (15)

To a solution of glycosyl donor 5 (1.24 g, 2.03 mmol) in $CH_2Cl_2$ (20 mL) was added 4 Å molecular sieves (2 g) and the mixture was stirred for 30 min at room temperature under argon atmosphere. BSP (511 mg, 2.44 mmol) and TTBP (727 mg, 2.92 mmol) were added at −60° C. followed by the addition of $Tf_2O$ (690 mg, 412 µl, 2.44 mmol) whereafter the reaction mixture was stirred under same conditions for 30 min. Compound 14 (800 mg, 1.69 mmol) in $CH_2Cl_2$ (10 mL) was added to the reaction mixture at −78° C. and stirred for 2 h at this temperature before quenching with Et₃N (1 mL). The reaction mixture was then filtered through a pad of celite followed by washing with $CH_2Cl_2$ (60 mL). The combined organic layer was washed with water (2×30 mL), brine (20 mL), dried ($Na_2SO_4$), concentrated and purified over $SiO_2$ to afford the 1-isomer 15 (930 mg, 57%) as a colorless foam. ESI-HRMS, Calcd. for $C_{53}H_{59}N_3O_{14}Na$ [M+Na]+: 985.0500. found: 984.3821.

3-Azidopropyl (2,3,4,6-tetra-O-acetyl-β-D-mannopyranosyl)-(1→2)-3,4,6-tri-O-acetyl-α-D-mannopyranoside (16)

To a stirred solution of compound 15 (800 mg, 0.832 mmol) and 1,3-propanedithiol (901 mg, 835 µL, 8.32 mmol) in $CH_2Cl_2$ (10 mL) was added TFA-$H_2O$ (5 mL, 4:1) at 0° C. and stirring was continued for 2 h at room temperature. The reaction mixture was diluted with water (15 mL) and washed with $CH_2Cl_2$ (4×15 mL) to remove all nonpolar organic materials. The aqueous layer was evaporated followed by co-evaporation with toluene (4×20 mL) under reduced pressure. The crude product was then dissolved in pyridine (15 mL) followed by the addition of $Ac_2O$ (10 mL) at 0° C. where after the reaction mixture was stirred at room temperature for 20 h. The solvents were evaporated under reduced pressure followed by co-evaporation with toluene (3×20 mL). The crude mixture was then purified over $SiO_2$ (hexane/EtOAc; 1:1) to afford the acetylated product 16 (365 mg, 61%) as a white powder. ESI-HRMS, Calcd. for $C_{29}H_{41}N_3O_{18}Na$ [M+Na]⁺: 742.6507. found: 742.2282.

1,2,3-tris[1-[(2,3,4,6-tetra-O-acetyl-β-D-mannopyranosyl)-(1→2)-(3,4,6-tri-O-acetyl-α-D-mannopyranosyloxypropyl)]-4-[methyl-1-oxy]triazolyl]propane (17)

To a solution of 8 (26.6 mg, 0.13 mmol) and 2-azidopropyl glycoside 16 (300 mg, 0.41 mmol) in $^tBuOH:H_2O:CH_2Cl_2$ (6 mL, 1:1:1, v/v/v) were added copper sulfate (6.3 mg, 0.042 mmol) and sodium ascorbate (15.4 mg, 0.08 mmol), respectively, and the mixture was heated at 55° C. for 12 h. Satd. $NH_4Cl$ and water (20 mL, 1:1) were poured into the solution followed by extraction with $CH_2Cl_2$ (3×20 mL). The organic layer was dried ($Na_2SO_4$), filtered, concentrated and purified over $SiO_2$ (4% MeOH in $CH_2Cl_2$) to afford the pure 17 (160 mg, 62%) as a colorless solid. ¹H NMR (600.13 MHz, $CDCl_3$) δ 7.69 (s, 1H), 7.63 (s, 2H), 5.48-5.47 (m, 3H), 5.26-5.21 (m, 6H), 5.05-5.03 (m, 3H), 4.96-4.93 (m, 3H), 4.77-4.73 (m, 8H), 4.63 (s, 4H), 4.49-4.45 (m, 6H), 4.34-4.28 (m, 6H), 4.34-4.22 (m, 3H), 4.04-4.00 (m, 6H), 3.87-3.85 (m, 3H), 3.79-3.76 (m, 1H), 3.76-3.73 (m, 3H), 3.68-3.64 (m, 7H), 3.48-3.37 (m, 3H), 2.23 (brs, 9H), 2.22-2.19 (m, 6H), 2.09 (br s, 9H), 2.08 (br s, 9H), 2.04 (br s, 9H), 2.02 (br s, 9H), 2.01 (br s, 9H), 1.99 (br s, 9H); ¹³C NMR (150.9 MHz, $CDCl_3$) δ 170.9 (3C), 170.6 (3C), 170.4 (3C), 170.3 (3C), 169.9 (3C), 169.6 (3C), 169.3 (3C), 145.6, 145.2 (2C), 122.9, 122.7 (2C), 97.8 (3C), 96.3 (3C), 77.3, 72.1 (3C), 72.0 (3C), 70.6 (3C), 70.3 (3C), 70.2 (2C), 68.7 (3C), 68.5 (3C), 66.1 (3C), 65.0 (3C), 64.8 (3C), 64.6 (2C), 63.8, 62.4 (3C), 61.8 (3C), 47.1 (3C), 30.0 (3C), 20.8 (6C), 20.7 (9C), 20.6 (6C); ESI-HRMS, Calcd. for $C_{99}H_{137}N_9O_{57}H$ [M+H]⁺: 2364.8100. found: 2364.8168.

Biological Tests of Synthetic β-1,2-Linked Mannooligosaccharide Compounds According to the Invention The β-1,2-linked mannooligosaccharide compounds according to the invention were next tested for their immunological activity. As the experiments were conducted by experts in the field of immunology, the samples have been renamed, documented and reported accordingly. The β-1,2-linked mannooligosaccharide compounds synthesized in previous experiments are referred to in the biological tests as follows:

CM-C8-2010 refers to β-1,2-linked mannooligosaccharide compound according to the preferred embodiment and described earlier as compound of formula IV and given in FIG. 2 as compound 9.

RP-I-82 2010 refers to β-1,2-linked mannooligosaccharide compound according to the another preferred embodiment and is tested for biological activity in example 4. The synthesis scheme for this compound is described in FIG. 4 and its structure as the end product 15.

Figure 7A:
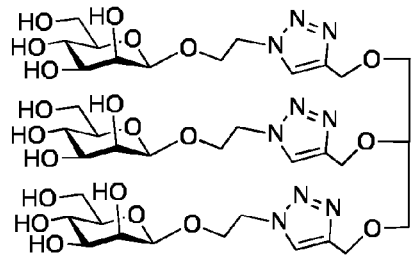
FIGS. 7a, 7b and 7c illustrate the chemical structures of mannooligosaccharide compounds used in Examples 1 and 2.
Figure 7C:
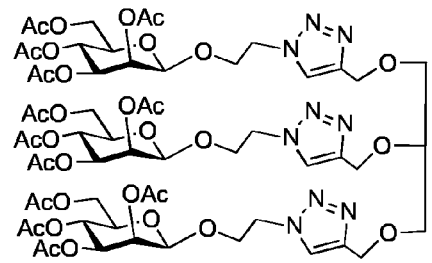
Figure 7B:
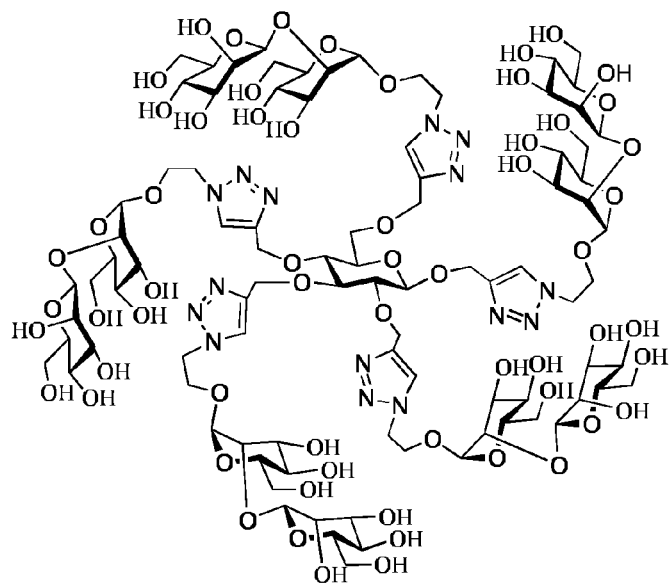

CM-C4-2010, CM-C7-2010 and CM-C4-2011 refer to structures given in FIG. 7a, FIG. 7b and FIG. 7c respectively.

In addition to cytokines discussed in description, the cell cultures were further tested for the effect on tumor necrosis factor TNF in example 4. TNF is a pleiotropic inflammatory cytokine that is expressed in mast cells and is present in higher concentrations in bronchioalveolar fluid from patients with asthma, particularly in bronchoalveolar lavage (BAL) fluid from patients with more severe asthma. It has been suggested as perhaps playing a role in refractory asthma.

Human PBMC

The human PBMC were isolated from heparinized blood samples with Ficoll (Ficoll-Paque, Amersham Pharmacia Biotech, Sweden) density gradient centrifugation. The PBMC were washed twice with Hanks' balanced salt solution (HBSS) and suspended in RPMI medium supplemented 5% autologous serum, 2 mM L-glutamine (Fluka Biochemica, Germany) and 100 g/ml gentamycin (Biological Industries, Israel). The cell suspension was diluted in the RPMI-based culture medium to $10^6$ cells/ml and applied on 48-well culture plates (Costar, Cambridge, Mass., USA).

Example 1

Induction of Cytokines by Synthetic β-1,2-Linked Mannooligosaccharide Compounds

Figure 5:
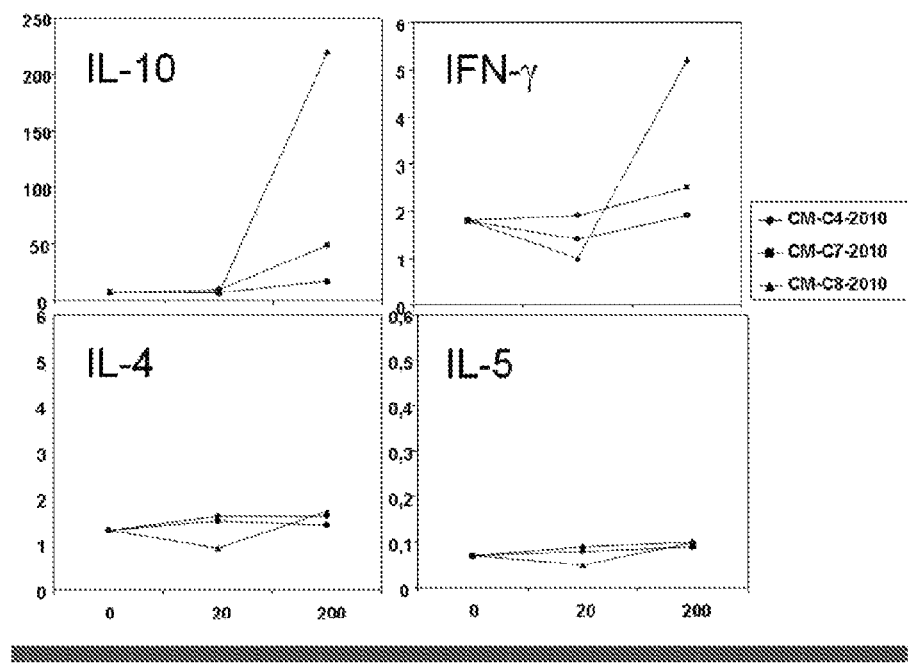
FIG. 5 shows cytokine production (vertical axis) induced by three chemically synthesized multivalent β-1,2-linked mannooligosaccharide compounds of the invention in human PBMC of three subjects assessed by LINCOplex™-kits using Luminex$^{100}$™ instrumentation. The horizontal axis gives the concentration, hence 20 and 200 μg/ml of each compound studied.

The synthetic oligosaccharides were tested for the production of cytokines IL-4, IL-5, IL-10 and IFN-γ, in peripheral blood mononuclear cells (PBMC) samples of three atopic subjects. The PBMC were stimulated by adding solubilized oligosaccharides in cell culture suspension. The synthetic polyvalent β-1,2-linked oligosaccharides used in this example are a molecule according to the compound of formula (IV) of the invention (coded CM-C8-2010), trivalent monosaccharide (R=H) coded CM-C4-2010 and pentavalent disaccharide (R=O) coded CM-C7-2010. The chemical structures of the CM-C4-2010 and CM-C7-2010 are shown in FIGS. 7a and 7b. The cytokine responses from PBMC were detected 72 h after beginning of the stimulation by measuring cytokine secretion with high-sensitivity human cytokine LINCOplex™-kits (LINCO Research, St. Charles, Mo., USA) using Luminex$^{100}$™ instrumentation. The assays were performed in accordance with the manufacturer's protocol by employing Luminex technology. Of the tested oligosaccharides a strong inducer of IFN-γ and IL-10 was a molecule according to the compound of formula (IV) of the invention coded CM-C8-2010, a moderate inducer a molecule coded CM-C7-2010 and a weak inducer a molecule coded CM-C4-2010 (FIG. 5). IL-4 and IL-5 production was not seen at all.

Example 2

Figure 6:
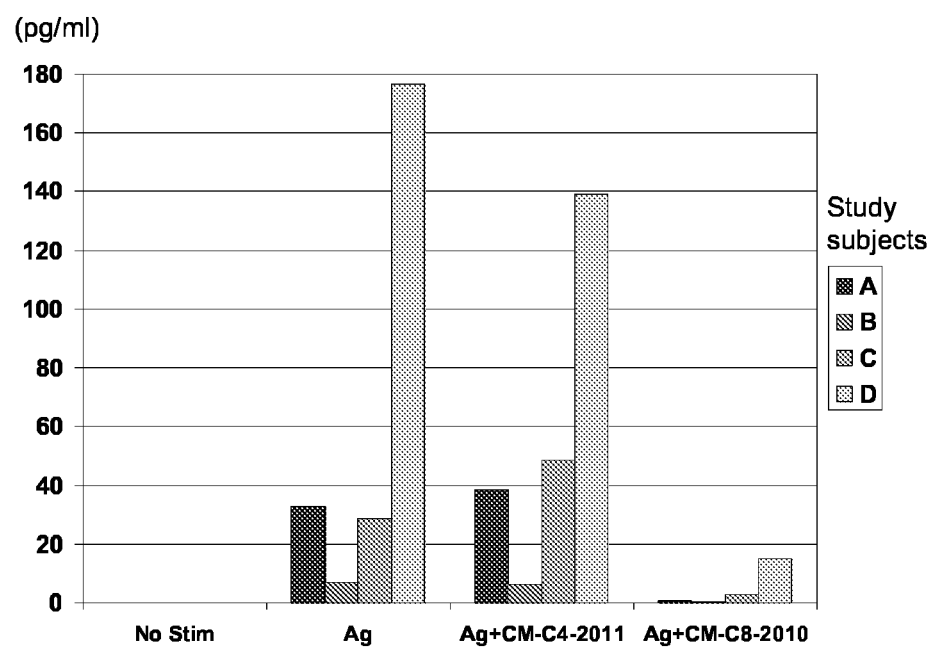
FIG. 6 shows suppression of allergen (Birch, Betula verrucosa) induced IL-5 production by two chemically synthesized multivalent β-1,2-linked mannooligosaccharide compounds in human PBMC from four study subjects (A, B, C, D) assessed by LINCOplex™-kits using Luminex$^{100}$™ instrumentation.

Effect of Synthetic β-1,2-Linked Mannooligosaccharide Compounds on Allergen-Induced Immune Response To show that the invention was valid, the effect of synthetic molecule according to the compound of formula (IV) of the invention coded CM-C8-2010 on the production of IL-5, one of the main Th2-type cytokine promoting allergic inflammation, was studied in an allergen (birch) stimulated PBMC culture of four birch allergic patients (A, B, C, D) with allergic rhinitis. Trivalent acetylated monosaccharide coded CM-C4-2011 was used as a negative control. The chemical structure of CM-C4-2011 is shown in FIG. 7c. The PBMC were isolated and cultured as described above. Birch whole allergen extract was used at a concentration of 50 g/ml and CM-C8-2010 at a concentration of 20 g/ml. The cultures were incubated for 72 hours. Following stimulation, the production of IL-5 was measured with LINCOplex™-kits using Luminex100™ instrumentation. In the cultures of all rhinitis patients CM-C8-2010 effectively suppressed the birch allergen induced IL-5 response whereas no suppression was seen with CM-C4-2011 (FIG. 6).

Example 3

Comparison of Synthetic β-1,2-Linked Mannooligosaccharide Compounds with Prior Art Adjuvants in Suppression of Allergen-Induced Immune Response The effect of synthetic molecule according to the compound of formula (IV) of the invention coded CM-C8-2010 on the production of IL-4, IL-5 and IL-13, the main Th2-type cytokines promoting allergic inflammation, was studied in an allergen (birch) stimulated PBMC culture of 26 birch allergic patients with allergic rhinitis. The effect was compared to that of 3-deacylated monophosphoryl lipid A (MPL), the non-toxic derivative of lipopolysaccharide of *Salmonella minnesota* (LPS), and immunostimulatory bacterial DNA sequence (CpG-ODN-1). These molecules have been clinically successfully tested as adjuvants in allergen immunotherapy. Another bacterial DNA sequence (CpG-ODN-2) without immunostimulatory activity was used as a negative control. The PBMC were collected during a strong birch pollen season, were isolated and cultured as described above. Birch whole allergen extract was used at a concentration of 50 g/ml and CM-C8-2010 at concentrations 200 and 20 g/ml. CpG-ODN-1 and CpG-ODN-2 were used at a concentration 5 g/ml and MPL at a concentration 10 g/ml based on earlier published experiments. The cultures were incubated for 24 hours. Following stimulation, the productions of IL-4, IL-5 and IL-13 were measured with LINCOplex™-kits using Luminex100™ instrumentation. For analysis only the cultures with strong induced cytokine responses were included. CM-C8-2010 suppressed the birch allergen induced IL-4, IL-5 and IL-13 responses more effectively than CpG-ODN-1 or MPL (Table 1). The suppressive effect was seen in higher number of subjects than with CpG-ODN-1 or MPL.

TABLE 1

| Mean (SD) percentage of Birch induced cytokine response | | | |
|---|---|---|---|
| | IL-4 | IL-5 | IL-13 |
| Number of subjects | 19 | 15 | 17 |
| CM-C8-2010; 200 µg/ml | 78.6 (24.3) | 70.6 (22.6) | 58.5 (48.0) |
| CM-C8-2010; 20 µg/ml | 90.8 (22.7) | 86.0 (25.9) | 85.9 (97.5) |
| CpG-ODN-1; 5 µg/ml | 139.8 (71.8) | 75.4 (29.7) | 73.3 (80.3) |
| CpG-ODN-2; 5 µg/ml | 99.5 (35.6) | 105.8 (38.8) | 92.7 (108.5) |
| MPL; 10 µg/ml | 88.0 (23.8) | 91.3 (20.6) | 61.6 (68.3) |

The results show that the compound according to the present invention provides better suppression in comparison to the prior art adjuvants. In this experiment the results further showed less inter patient variation for the compound according to the present invention than for the prior art compounds. Allergic reactions are dependent on several responses and are affected by a number regulatory factors. Therefore, when CpG-ODN-1 provides a slight response with respect to IL-5 and IL-13, the response to IL-4 is poor. In comparison to this, result obtained with a compound of the invention is very promising, as such characteristics predict better expectation of therapy and suitability to most patients.

Example 4

Induction of Cytokines by Synthetic Oligosaccharide

The synthetic oligosaccharide coded RP-I-82 was tested for the production of cytokines IL-4, IL-5, IL-10, IL-13, TNF and IFN-γ, in peripheral blood mononuclear cells (PBMC) samples of three subjects. The PBMC were stimulated by adding solubilized oligosaccharide in cell culture suspension. The synthetic oligovalent 3-1,2-linked oligosaccharide used in this example was a molecule according to the compound of formula (IV) of the invention (coded RP-I-82). The synthesis scheme and chemical structure of the RP-I-82 is shown in FIG. 2 (compound 9). A positive control was acid hydrolyzed *Candida albicans* mannan (CAM). The cytokine responses from PBMC were detected 24 hours after beginning of the stimulation by measuring cytokine secretion with high-sensitivity human cytokine LINCOplex™-kits (LINCO Research, St. Charles, Mo., USA) using Luminex$^{100}$™ instrumentation. The assays were performed in accordance with the manufacturer's protocol by employing Luminex technology. The tested oligosaccharide was a strong inducer of IL-10 and TNF and a moderate inducer of IFN-γ (Table 2). IL-4, IL-5 and IL-13 production was not seen at all.

TABLE 2

Production of cytokines (pg/ml), mean (SD).

|  | IL-4 | IL-5 | IL-13 | IL-10 | IFN-γ | TNF |
| --- | --- | --- | --- | --- | --- | --- |
| No stimulation | 2.0 (0.6) | 0.0 (0.0) | 0.5 (0.0) | 7.7 (4.4) | 1.3 (0.4) | 18 (14) |
| RP-I-82; 20 µg/ml | 2.6 (0.8) | 0.1 (0.2) | 0.6 (0.2) | 110 (109) | 10 (15) | 52 (26) |
| RP-I-82; 200 µg/ml | 2.7 (0.2) | 0.2 (0.2) | 0.5 (0.0) | 843 (253) | 18 (25) | 295 (146) |
| CAM; 200 µg/ml | 61 (36) | 20 (2.2) | 48 (8.4) | 193 (11) | 727 (901) | 156 (158) |

From these results, it can be concluded that the compound according to the present invention (RP-I-82) provides cytokine-specific induction of IL-10, IFN-γ and TNF production in cell culture suspension. For IL-10 and TNF this was considerably higher than for the control, *Candida albicans* mannan (CAM). It is also noteworthy, that said control, CAM induced all cytokines in comparison to the blank sample (no stimulation), whereas the compound according to the present invention (RP-I-82) provided selective induction an important role in down-regulation of Th2-type responses towards allergens.

REFERENCES

Alpe M, Oscarson S, Svahnberg P (2003) Synthesis of *cryptococcus neoformans* capsular polysaccharide structures. IV. Construction of thioglycoside donor blocks and their subsequent assembly. J Carbohydr Chem 22:565-577.

Ballell L, van Scherpenzeel M, Buchalova K, Liskamp R M J, Pieters R J (2006) A new chemical probe for the detection of the cancer-linked gelectin-3. Org Biomol Chem 4:4387-4394.

Bentz E L, Gibson H, Hudson C, Moloney M G, Seldon, D A, Wearmouth E S (2006) Aryldiazirine-modified pyroglutamates: Photoaffinity labels for glutamate. Synlett 247-250.

Bocks K, Pedersen C (1974) A study of $^{13}$CH coupling constants in hexopyranoses. J Chem Soc Perkin Trans 2, 293-297.

Codee J D C, Hossain L H, Seeberger P H (2005) Efficient installation of β-mannosides using a dehydrative coupling strategy. Org Lett 7:3251-3254.

Crich D, Li H (2000) Direct stereoselective synthesis of β-thiomannosides. J Org Chem 65:801-805.

Crich D, Smith M J (2001) 1-Benzenesulfinyl piperidine/trifluoromethanesulfonic anhydride: A potent combination of shelf-stable reagents for the low-temperature conversion of thioglycosides to glycosyl triflates and for the formation of diverse glycosidic linkages. J Am Chem Soc 123:9015-9020.

Crich D, Li H (2002) Synthesis of the *Salmonella* Type $E_1$ core trisaccharide as a probe for the generality of 1-(benzenesulfinyl)piperidine/triflic anhydride combination for glycosidic bond formation from thioglycosides. J Org Chem 67:4640-4646.

Crich D, Jayalath P, Hutton K T (2006) Enhanced diastereoselectivity in β-mannopyranosylation through the use of sterically minimal propargyl ether protecting groups. J Org Chem 71:3064-3070.

de Paz J L, Martin-Lomas M (2005) Synthesis and biological evaluation of a heparin-like hexasaccharide with the structural motifs for binding to FGF and FGFR. Eur J Org Chem 9:1849-1858.

The International Study of Asthma and Allergies in Childhood (ISAAC) Steering Committee (1998) Worldwide variations in the prevalence of symptoms of asthma, allergic rhinoconjunctivitis and atopic eczema. Lancet 351: 1225-32.

Maezaki N, Kojima N, Sakamoto A, Tominaga H, Iwata C, Tanaka T, Monden M, Damdinsuren B, Nakamori S (2003) Total Synthesis of the antitumor acetogenin Mosin B: Desymmetrization approach to the stereodivergent synthesis of threo/trans/erythro-type Acetogenins. Chem Eur J 9:389-399.

Matsuda H, Zhang S, Holmes A E, Krane S, Itagaki Y, Nakanishi K, Nesnas N (2006) Synthesis of an 11-cis-locked biotinylated retinoid for sequestering 11-cis-retinoid binding proteins. Can J Chem 84:1363-1370.

Mourer M, Hapiot F, Tilloy S, Monflier E, Menuel S (2008) Easily accessible mono- and polytopic β-cyclodextrin hosts by click chemistry. Eur J Org Chem 5723-5730.

Ohlsson J, Magnusson G (2000) Galabiosyl donors; efficient synthesis from 1,2,3,4,6-penta-O-acetyl-β-D-galactopyranose. Carbohydr Res 329:49.

Pfaendler H R, Weimar V (1996) Synthesis of racemic ethanolamine plasmalogen. Synthesis 1345-1349.

Pérez-Balderas F, Hernández-Mateo F, Santoyo-González F (2005) Synthesis of multivalent neoglycoconjugates by 1,3 dipolar cycloaddition of nitrile oxides and alkynes and evaluation of their lectin-binding affinities. Tetrahedron 61:9338-9348.

Soderquist J A, Brown H C (1980) Hydroboration. 56. Convenient and regiospecific route to functionalized organosilanes through the hydroboration of alkenylsilanes. J Org Chem 45:3571-3578.

The invention claimed is:

1. An immunostimulatory compound of formula (II)

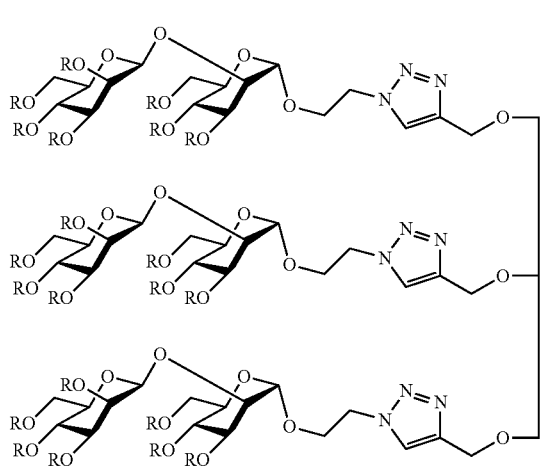

(II)

wherein each R is independently selected from acetyl (COCH₃), hydrogen (H), trifluoroacetyl (COCF₃) or sulfonate group or other ester group.

2. The immunostimulatory compound according to claim 1, wherein each R is acetyl (COCH₃).

3. A method for immunostimulating a subject, comprising:
administering the immunostimulatory compound according to claim 1 to a subject in need of immunostimulating.

4. A method for immunostimulating a subject, comprising:
administering a composition comprising an adjuvant of a vaccine which comprises an effective amount of the immunostimulatory compound according to claim 1 and a vaccine component to a subject in need of immuno stimulating.

5. A method for inducing a Treg- and/or Th1-type, and/or inhibiting a Th2-type immune response, comprising:
administering the immunostimulatory compound according to claim 1 to a subject in need of inducement of a Treg- and/or Th1-type, and/or inhibition of a Th2-type immune response.

6. The method of claim 3, wherein the subject has type I immediate atopic allergy.

7. The method of claim 3, wherein the subject has a condition selected from the group consisting of
a) atopic eczema/dermatitis syndrome (AEDS),
b) allergic asthma,
c) allergic rhinitis
d) allergic urticaria,
e) food allergy,
f) venom allergy, and
g) allergic rhinoconjunctvitis.

8. The method of claim 3, wherein the subject has a condition that is an infectious disease.

9. An immunostimulatory composition comprising the immunostimulatory compound according to claim 1, and a pharmaceutically acceptable carrier.

10. The immunostimulatory composition according to claim 9, wherein the pharmaceutically acceptable carrier is a transmucosal carrier for sublingual and/or buccal administration.

11. The immunostimulatory composition according to claim 9, wherein it further comprises an allergen preparation for specific allergen immunotherapy; and/or an additional allergy or asthma medicament.

12. The immunostimulatory composition according to claim 9, wherein it further comprises a microbe-specific antigen for vaccination against infectious disease; and/or an antimicrobial agent.

13. A food additive or a nutritional preparation comprising the immunostimulatory compound according to claim 1 in a food additive or a nutritional preparation.

14. The immunostimulatory composition according to claim 9, wherein the pharmaceutically acceptable carrier is selected from the group consisting of transdermal carriers, transmucosal carriers, oral carriers, parenteral carriers, carriers for depot formulations, and carriers for extended release formulations.

* * * * *